United States Patent [19]

Aeppli

[11] Patent Number: 5,499,794
[45] Date of Patent: Mar. 19, 1996

[54] PROCESS AND DEVICE FOR DETECTING FOREIGN SUBSTANCES IN A TEXTILE TEST MATERIAL USING AN ALTERNATING LIGHT AND DARK BACKGROUND

[75] Inventor: Kurt Aeppli, Uster, Switzerland

[73] Assignee: Zellweger Luwa AG, Switzerland

[21] Appl. No.: 297,843

[22] Filed: Aug. 30, 1994

[30] Foreign Application Priority Data

Sep. 9, 1993 [CH] Switzerland ............... 02705/93

[51] Int. Cl.$^6$ ................................. G01N 21/88
[52] U.S. Cl. ................. 250/559.45; 250/559.41; 356/430; 73/160
[58] Field of Search ................ 250/562, 572, 250/561, 559.45, 599.40, 559.41; 356/430, 429, 238; 73/160

[56] References Cited

U.S. PATENT DOCUMENTS

| | | | |
|---|---|---|---|
| 4,184,769 | 1/1980 | Aeppli | 356/430 |
| 4,739,176 | 4/1988 | Allen et al. | 250/572 |
| 5,054,317 | 10/1991 | Laubscher | 73/160 |
| 5,371,584 | 12/1994 | Scheinhütte | 356/238 |
| 5,383,017 | 1/1995 | Schürch | 356/238 |

Primary Examiner—Edward P. Westin
Assistant Examiner—Stephen Calogero
Attorney, Agent, or Firm—Burns, Doane, Swecker & Mathis

[57] ABSTRACT

Test material (F) such as a textile yarn is illuminated and the light reflected from the test material is measured so that the presence of a foreign substance can be determined from a change in the reflected light. When detecting foreign substances which are darker than the test material (F), an image of the test material in front of a light background (4) is projected onto a sensor (3), and for the detection of lighter foreign substances an image of the test material in front of a dark background is projected onto the sensor. The apparatus and method may be used in combination with an electronic yarn clearer for the purpose of detecting foreign fibers in yarns.

17 Claims, 1 Drawing Sheet

PROCESS AND DEVICE FOR DETECTING FOREIGN SUBSTANCES IN A TEXTILE TEST MATERIAL USING AN ALTERNATING LIGHT AND DARK BACKGROUND

FIELD OF THE INVENTION

This invention relates to apparatus and processes for detecting foreign substances in textile test material such as yarns, rovings or slivers. The test material is subjected to light, the light reflected from the test material is measured, and the presence of a foreign substance is concluded from a change in the reflected light.

BACKGROUND

A process for detecting contaminants in yarn is disclosed in EP-A-0,197,763, and its counterpart U.S. Pat. No. 4,739,176. In this process, a background surrounds the test material in the manner of a guide slot and is subjected to light. The background is coordinated with the test material in such a way that the total quantity of light reflected from the test material and of light coming from the background is independent of the dimensions and density of the test material and on the distribution of the fibers within the latter. It is intended to be possible in this way for a variation in the reflected light to indicate a foreign substance and not a variation in the dimensions, the density or the fiber distribution in the test material.

In this process, whenever the kind or type of test material is changed, relatively complex adjustment work is necessary to adapt the background to the test material. Also, the process is highly sensitive to contamination and aging of the background. Moreover, both of these are phenomena which are not only unavoidable in a textile concern but frequently occur in that very environment.

OBJECTS AND SUMMARY OF THE INVENTION

Objects of the present invention are to provide apparatus and processes for detecting foreign substances in yarns, rovings and slivers, which are not subject to requirements for special coordination of the background with the test material and in which the complex adjustment formerly required is not necessary.

According to the invention, an image of the test material is projected onto a sensor in front of a light background for the detection of foreign substances darker than test material and in front of a dark background for the detection of lighter foreign substances. The signal developed in the sensor is compared with adjustable limit values so that, in the first case, an undershooting of the respective limit value and, in the second case, an overshooting of the respective limit value by the signal is interpreted as indicating the presence of the foreign substance sought.

The process according to the invention is based on the fact that foreign substances are for the most part either lighter or darker than the test material and therefore can be sensed relatively simply by imaging in front of a contrasting background.

The invention relates, furthermore, to a device or apparatus for carrying out the said process, with means for illuminating the test material and with a light-sensitive sensor. The device according to the invention is characterized in that the sensor is formed by a line sensor and in that an optionally illuminatable or non-illuminatable background is provided.

The line sensor has the advantage that the image field is resolved into a multiplicity of elements, so that any foreign substances which extend only over a small part of the diameter of the test material yield a sharp contrast in one or more picture elements and therefore can be well detected. Devices with a sensor which comprise only a single element, on the other hand, provide in this case only a very low contrast and are greatly restricted in their sensitivity. Compared to systems with image processing, the signal evaluation is restricted to a simple threshold detection, so that the hardware and software outlay are minimal.

A preferred embodiment of the device according to the invention is characterized in that the background is formed by a ground glass screen and in that a light source is provided for the optional illumination of the ground glass screen.

BRIEF DESCRIPTION OF THE DRAWINGS

The invention is explained in more detail below by means of an exemplary embodiment and the drawings, in which.

DETAILED DESCRIPTION OF PREFERRED EMBODIMENT

Figure 1:
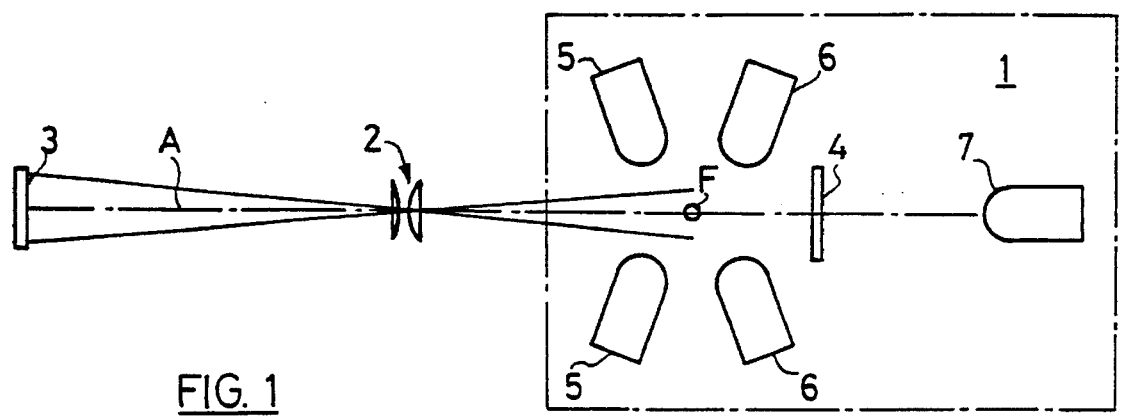
FIG. 1 shows a diagrammatic representation of a device according to the invention.

Apparatus is represented in FIG. 1 for detecting foreign substances in an elongate textile test material, in particular in yarns. In this view the thread F to be examined should be understood to be moving along a vertical line extending perpendicular to the paper. The detection apparatus comprises an illumination unit 1 through which the vertically disposed thread F to be examined passes at right angles with respect to a horizontal image plane. Light reflected from the thread F passes to an objective 2, and the objective 2 projects an image of the thread F onto a line sensor 3.

The illumination unit 1 includes a ground glass screen 4 lying on the optical axis A of the device and forming the background for the imaging of the thread F. A direct-light illuminating means 5 is provided for illuminating the thread F obliquely from the front, and a back-light illuminating means 6 is provided for illuminating the thread F obliquely from the rear. The ground glass screen 4 is illuminated from the rear by a transmitted-light illuminating means 7. The illumination of the thread F with direct light and back light allows the thread to appear as uniformly as possible, the back light in particular lighting up the marginal zones of the thread F, which would otherwise appear too dark.

The transmitted-light illuminating means 7 serves to illuminate the ground glass screen 4 as uniformly as is possible, so that when there is no thread F, the signals of all the photodiodes of the line sensor 3 are approximately the same. With illumination of the ground glass screen 4 by the transmitted-light illuminating means 7, the thread F runs in front of a light background. As a result, foreign substances which are darker than the thread can be sensed by the line sensor 3. For the detection of foreign substances which are lighter than the thread F, the transmitted-light illuminating means 7 is switched off.

For the sensing of both lighter and darker foreign substances, the background of the thread F is alternately illuminated and not illuminated. That is to say, the transmitted-light illuminating means 7 is alternately switched off and on. In this case, the clock frequency is adapted to the thread speed in such a way that the pieces of yarn sensed in each case overlap one another.

The use of the line sensor 3 makes it possible to evaluate only the signal components originating from the core of the thread F under examination. As a result, the influence of changes in the diameter of the examined thread on the sensor signal is eliminated. The line sensor may have 128 pixels, for example, so that the image field is divided into 128 elements. Any foreign substances which extend only over a small part of the thread diameter yield a great contrast in one or more of the picture elements and are therefore reliably detected.

Light-emitting diodes, for example those of a particular color such as green or red, are used as illuminating elements. Alternatively, if the light provided by light-emitting diodes is not adequate for the thread speed required, lasers or flashlamps or incandescent lamps may be used. A light-emitting diode multichip arrangement with special illuminating optics may also be used and operated in a pulse mode.

Figure 2:
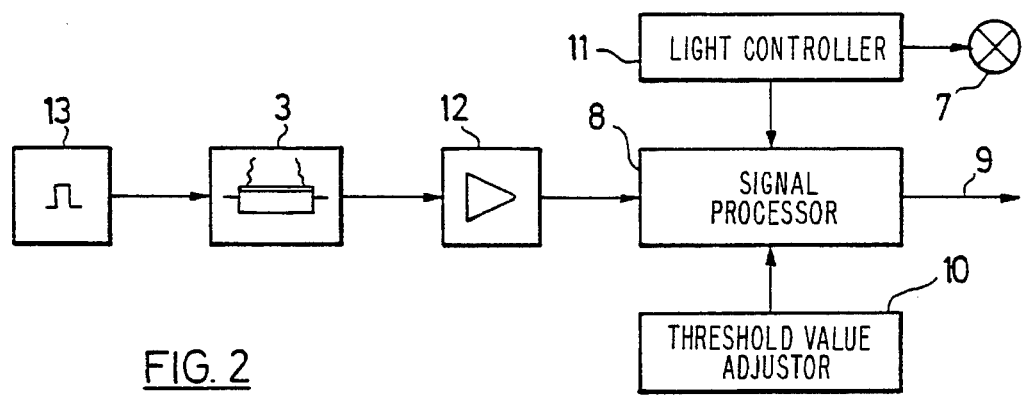
FIG. 2 shows a diagram of a circuit of a device according to FIG. 1.

According to FIG. 2, the circuit of the device represented in FIG. 1 includes a processing stage or unit 8. Two adjustable threshold values, one for lighter foreign substances and one for darker foreign substances, are stored in the signal processor 8. In the event of overshooting of the threshold value for the lighter foreign substances and undershooting of the threshold value for the darker foreign substances, the processor 8 in each case emits via a line 9 a foreign-substance signal. The foreign substance signal may be employed to initiate appropriate measures, such as, for example, a clearer operation for effecting removal from the yarn of the yarn portion containing the foreign substance. The two threshold values are adjustable by means of an adjusting unit or stage 10 connected to the processing stage 8. The alternate switching on and off of the transmitted-light illuminating means 7 is controlled by a control unit or stage 11 which is also connected to the processing stage 8 and, for each illuminating state of the transmitted-light illuminating means 7 the associated threshold switch is activated. At a further input of the processing stage 8 there lies the output of an amplifier 12, amplifying the signal of the line sensor 3. The time sequence of the operations of the line sensor 3 is controlled by a clock generator 13.

Figure 3:
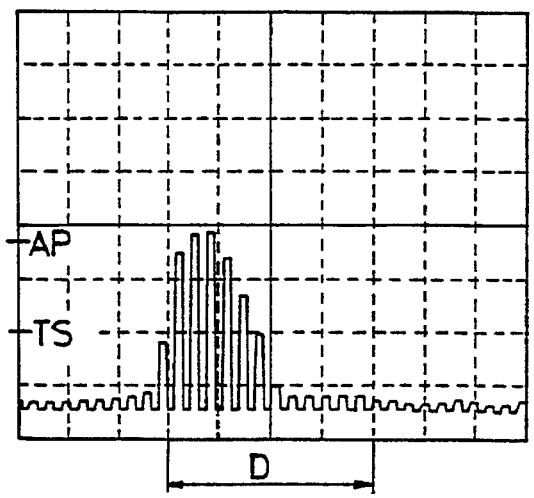
FIGS. 3 and 4 show diagrams for functional explanation.
Figure 4:
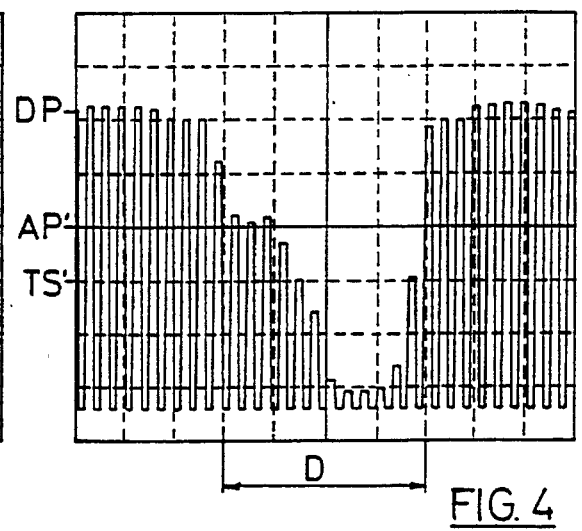

FIGS. 3 and 4 show examples of the detection of foreign substances with the device or circuit represented in FIGS. 1 and 2, to be precise by showing the signals supplied by the line sensor 3 in the examination of a twine comprising a white yarn and a black yarn. In the diagrams, the direction transverse to the twine is plotted on the x axis and the signal amplitude is plotted on the y axis. The range on the line sensor 3 corresponding to the twine diameter is denoted by the reference symbol D.

FIG. 3 shows the sensor signal with transmitted-light illuminating means 7 switched off, that is to say with a dark background. The black thread produces virtually no signal in the second half of the twine diameter, whereas the white thread provides a distinct foreign-substance signal in the first half. In the figure, AP denotes the direct-light level and TS denotes the triggering threshold for overshoots.

FIG. 4 shows the sensor signal with transmitted-light illuminating means 7 switched on, that is to say, with a light background. Here the black thread provides a foreign-substance signal which can be seen as a sharp dip. The signal components with the level DP outside the range D corresponding to the twine diameter are caused by the transmitted-light illuminating means 7, which in the case of the example shown is stronger than the direct-light and back-light illumination (level AP') together. Consequently, the ratio of the illumination is chosen such that the white thread emits less of a signal than the empty thread guide without a thread. TS' denotes the triggering threshold for undershoots.

In the "empty" state of the device without a thread, with transmitted-light illuminating means 7 switched on, it is possible to store in analog or digital form the intensity value for each element of the diode line. In operation, the measurements with the test material F are related element by element to the stored values; the offset is thus subtracted element by element. This mode of operation has the advantage of compensating for inhomogeneities in the background illumination and avoiding errors caused by individual diode line elements of lesser photosensitivity.

Moreover, there is compensation for soiling slowly building up on the measuring field, which results in additional inhomogeneities in the transmitted light. In the empty state a value for the soiling of the light-exposed parts of the device is derived from the light intensity and/or the brightness profile and a corresponding alarm is set.

The direct-light and/or back-light illuminating means 5 and 6, respectively, is preferably calibrated before being put into operation by storing element by element the light intensity maxima when entering a test piece as similar as possible to the yarn to be tested. The offset compensation is performed precisely as just described for the transmitted-light illuminating means 7.

The device described with reference to FIGS. 1 and 2 for detecting impurities in a yarn is designed as a compact measuring head and is preferably used in combination with an electronic yarn clearer (see EP-B-0,197,763 in this respect), the cutting device of which is also controlled, in addition to the measuring head of the cleaner, by the measuring head for the impurities.

The measuring head may be designed such that a plurality of functions, that is to say, for example, yarn clearing, hairiness measurement and the detection of foreign fibers, can be performed by means of a single optical scanning device. A measuring head suitable for this purpose, with a line sensor, is described in CH-A-643,060 and its counterpart GB 2064106. In the case of this measuring head, the individual photoelements of the line sensor are scanned. As a result a time resolution of the diameter image or cross-section image of the examined fiber is achieved in the form of a pulse sequence which can he directly used in many ways for the further digital measured-value processing. Similarly, it is possible with a combined capacitive/optical measuring member of the type described in EP-A-0,401,600 and its counterpart U.S. Pat. No. 5,054,317 to measure capacitively the yarn defects for the purpose of yarn clearing and optically for the purposes of determining the hairiness of the yarn and the reflections representative of foreign fibers.

A configuration as an integrated photo-ASIC with control electronics for blanking and/or with evaluation electronics is also possible. Here, even a parallel processing of the diode-line signals in which each element has its own amplifier and its own offset compensation, including analog storage of the offsets, would be possible. The threshold value for the foreign-fiber detection is in this case set jointly for all the elements.

What is claimed is:

1. A process for detecting in a moving yarn foreign material lighter or darker than the yarn, comprising moving the yarn along a path in front of a background that is dark and light at alternate times, illuminating the portion of the yarn passing in front of the background, and focussing an image of the yarn passing in front of the background onto a sensor so that a change in reflected light due to the passage of foreign material may be detected.

2. Process for detecting foreign substances in a textile test material comprising projecting onto a sensor images of a test material in front of both a light background for the detection of foreign substances that are darker than the test material and in front of a dark background for the detection of foreign substances that are lighter than the test material, and comparing signals produced by said sensor with one limit value which is appropriate for detecting the presence of a lighter foreign substance against the dark background and with another limit value which is appropriate for detecting the presence of a darker foreign substance against the light background to determine the presence of a foreign substance when the signals overshoot said one limit value or when the signals undershoot said another limit value.

3. Process according to claim 2, wherein for the detection of darker and lighter foreign substances, the background is alternately illuminated and not illuminated.

4. Process according to claim 3, wherein switching to the respective limit value is carried out synchronously with changing between illumination and non illumination of the background.

5. Process according to claim 2, including adjusting said one limit value and said another limit value.

6. Apparatus for detecting foreign substances in a textile test material that is moving along a movement path comprising an alternately illuminated and non-illuminated background positioned adjacent a portion of the movement path, means for illuminating a portion of the test material passing in front of said background during both illumination and non-illumination of the background and a light-sensitive line sensor for receiving images formed at least in part by light reflected from said portion of the test material during the illumination and non-illumination of the background.

7. Apparatus according to claims 6, wherein the background is formed by a ground glass screen, and including a light source for alternately illuminating and non-illuminating the ground glass screen.

8. Apparatus according to claim 7, including a signal processor for receiving signals from said line sensor via an amplifier for synchronously evaluating such signals with reference to two different threshold values, one of the threshold values being selected to be appropriate for the detection of dark foreign matter against a light background and the other threshold value being selected to be appropriate for the detection of light foreign matter against a dark background.

9. Apparatus according to claim 7, wherein said light source is arranged on a side of the ground glass screen facing away from the line sensor.

10. Apparatus according to claim 9, including a signal processor for receiving signals from said line sensor via an amplifier for synchronously evaluating such signals with reference to two different threshold values, one of the threshold values being selected to be appropriate for the detection of dark foreign matter against a light background and the other threshold value being selected to be appropriate for the detection of light foreign matter against a dark background.

11. Apparatus according to claim 6, wherein said means for illuminating the test material includes a direct-light illuminating means and a back-light illuminating means.

12. Apparatus according to claim 11, wherein said means for illuminating the test material includes one of light-emitting diodes, laser diodes, flashlamps and incandescent lamps.

13. Apparatus for detecting foreign material in a moving yarn, comprising a background disposed opposite a portion of the path of the yarn;

means for illuminating a portion of the yarn passing in front of said background;

a sensor for receiving an image formed in part by light reflected from said portion of said yarn and in part by light from said background; and a light source for alternately illuminating and not illuminating said background while said portion of said yarn is passing in front of said background so that dark foreign matter in said yarn will be detected against a light background and light foreign matter in said yarn will be detected against a dark background.

14. Apparatus according to claim 13, wherein said sensor is a line sensor having a length much greater than the width of said yarn.

15. Apparatus according to claim 14, wherein said background is translucent and said light source is located on the side of said background opposite the yarn and is switched on and off repetitively.

16. Apparatus according to claim 15 including a signal processor receiving signals from said sensor for synchronously evaluating such signals with reference to two different threshold values, one of which is selected to be appropriate for the detection of dark foreign matter against a light background and the other of which is selected to be appropriate for the detection of light foreign matter against a dark background.

17. Apparatus according to claim 13, wherein said background is translucent and said light source is located on the side of said background opposite the yarn and is switched on and off repetitively.

* * * * *